United States Patent [19]

Jensen

[11] 4,445,898
[45] May 1, 1984

[54] FECAL INCONTINENCE DEVICE WITH SEPARABLE RELEASE SHEETS

[75] Inventor: Marvin E. Jensen, Niles, Ill.

[73] Assignee: Hollister Incorporated, Libertyville, Ill.

[21] Appl. No.: 358,690

[22] Filed: Mar. 16, 1982

[51] Int. Cl.³ .............................................. A61F 5/44
[52] U.S. Cl. .................................. 604/337; 604/332; 604/338
[58] Field of Search ............... 604/317, 327, 332, 333, 604/334, 337–339, 341, 342, 344, 336, 348, 355; 128/760, 767; 4/144.2, 144.3; 206/86; 55/DIG. 2

[56] References Cited

U.S. PATENT DOCUMENTS

| | | | |
|---|---|---|---|
| 2,491,799 | 12/1949 | Clarke | 128/283 |
| 2,679,248 | 5/1954 | Fullaway | 604/337 |
| 2,928,393 | 3/1960 | Marsan | 604/334 |
| 3,221,742 | 12/1965 | Orowan | 604/339 |
| 3,292,626 | 12/1966 | Schneider | 128/295 |
| 3,421,506 | 1/1969 | Priebe et al. | 4/144.3 |
| 3,522,807 | 8/1970 | Millenbach | 128/283 |
| 3,577,989 | 5/1971 | Anderson | 128/283 |
| 3,734,096 | 5/1973 | Millenbach | 128/283 |
| 3,952,336 | 4/1976 | Kunter | 4/112 |
| 4,219,023 | 8/1980 | Galindo | 604/344 |
| 4,253,460 | 3/1981 | Chen et al. | 604/344 |
| 4,274,847 | 6/1981 | Crener | 55/DIG. 2 |

FOREIGN PATENT DOCUMENTS

| | | | |
|---|---|---|---|
| 719111 | 10/1965 | Canada | 604/338 |
| 1085927 | 10/1967 | United Kingdom . | |
| 1092274 | 11/1967 | United Kingdom . | |
| 2000683 | 1/1979 | United Kingdom . | |
| 2017501 | 4/1979 | United Kingdom . | |
| 2082916 | 3/1982 | United Kingdom . | |

Primary Examiner—C. Fred Rosenbaum
Assistant Examiner—J. L. Kruter
Attorney, Agent, or Firm—Tilton, Fallon, Lungmus

[57] ABSTRACT

A fecal incontinence device in the form of an elongated collection bag having an attachment ring about an opening at one end of the bag. The ring is formed of a soft, pliable, and stretchable closed-cell thermoplastic foam, and the bag is formed from a single sheet or film of thermoplastic material that, following its attachment to the ring, is folded to provide a pair of side panels extending at right angles to the plane of the ring, such panels then being heat sealed to each other along their margins to define the finished bag. The foam attachment ring has its surface coated with a pressure-sensitive adhesive, and its inner and outer margins are non-concentric to define a relatively narrow perineal attachment zone. A plurality of release sheet sections cover the adhesive coating of the ring and are sequentially removable to facilitate effective attachment of the ring to a patient. The bag is also provided with a protected gas vent and a self-closing passage for the insertion of a thermometer or other medical instrument.

17 Claims, 12 Drawing Figures

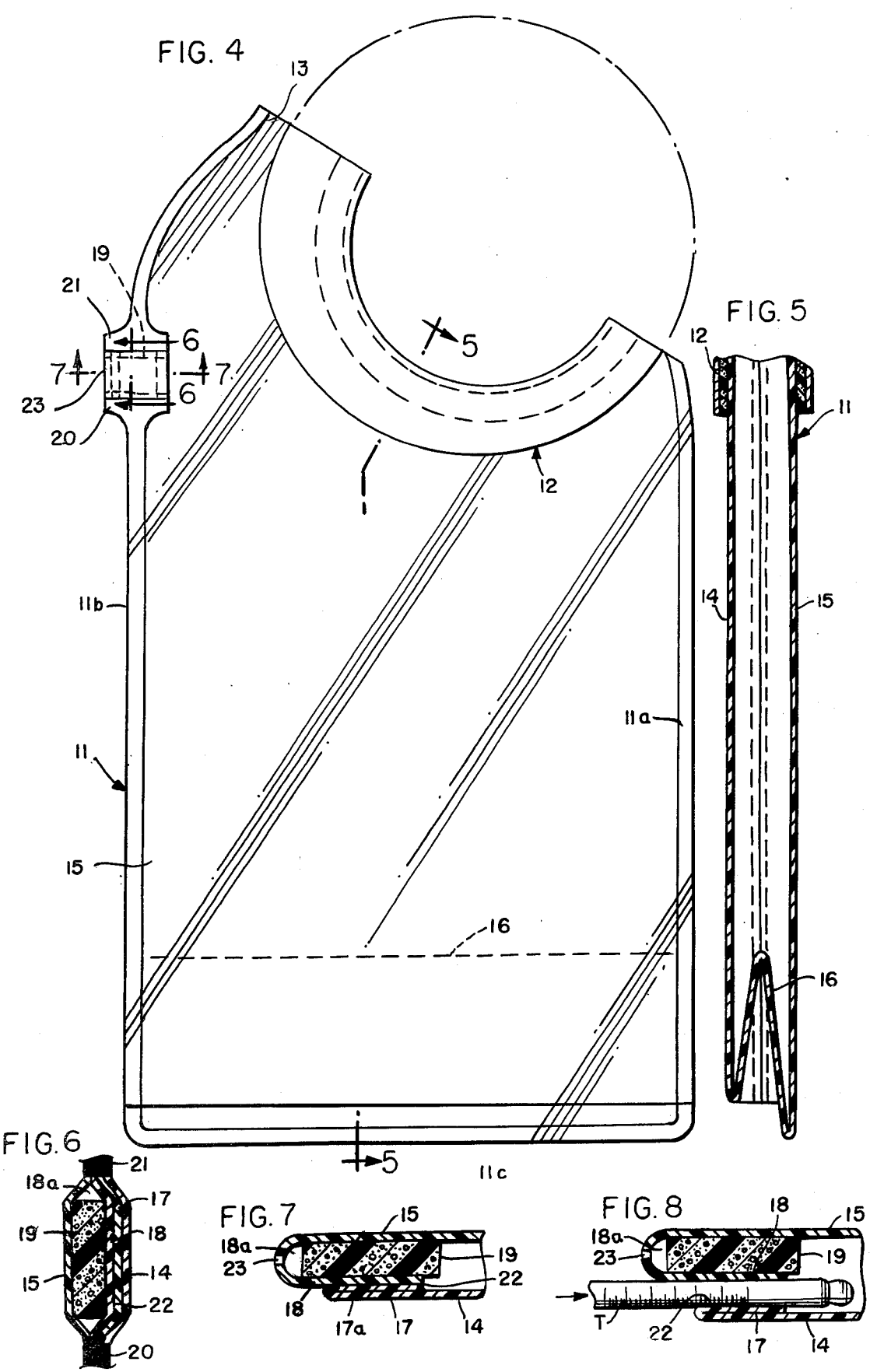

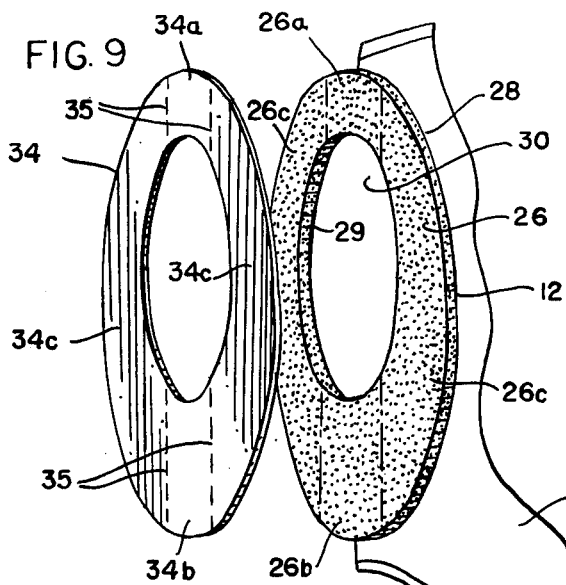
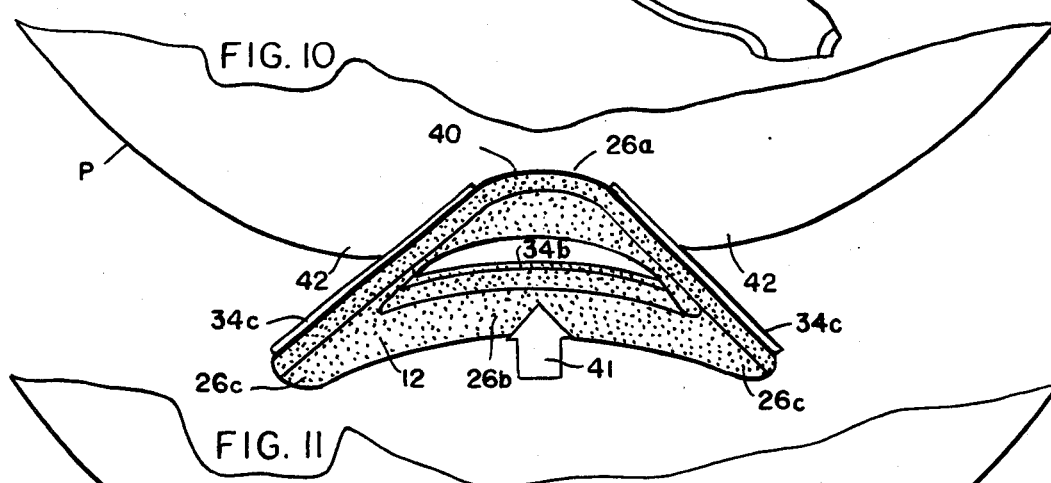
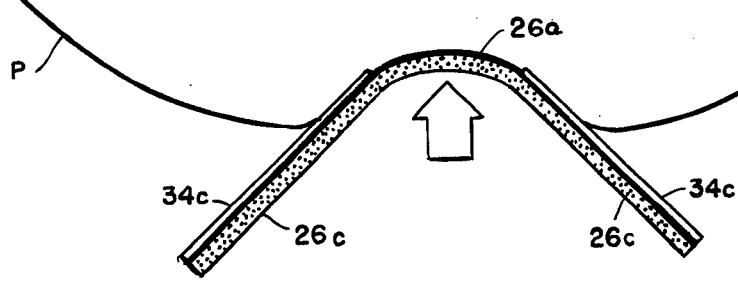
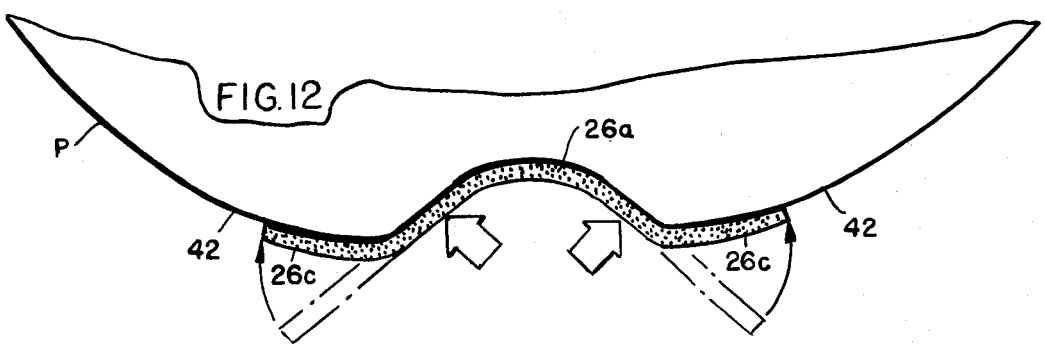

FECAL INCONTINENCE DEVICE WITH SEPARABLE RELEASE SHEETS

BACKGROUND AND SUMMARY

While collection bags for incontinent patients are known in the art, such devices have not been free of serious shortcomings. One major problem concerns the formation of an effective external seal about the rectum; various types of adhesive rings have been disclosed but no single design is known for its ease of application and removal, freedom from leakage and unintentional detachment, and adaptability, comformability, and comfort in use. U.S. Pat. Nos. 3,577,989 and 2,491,799 disclose collection bags which are strapped to patients. The manipulation of such straps during attachment and detachment, and the need to move or reposition a patient during such operations, complicates the use of such devices and increases patient inconvenience and discomfort. Devices with adhesive-coated attachment rings, such as disclosed in U.S. Pat. Nos. 3,577,989, 3,734,096, 3,522,807, 3,952,336, and 3,292,626 are also difficult to affix, at least if an effective seal is to be formed, because of the varying contours, and the stretchability, contractability, and softness, of the perianal surfaces. Making adequate sealing contact is only one problem; maintaining such contact is another. If the adhesive used to retain such collectors is aggressive enough to prevent accidental detachment, such collectors may be relatively difficult to remove without causing patient discomfort. Conversely, if a less aggressive adhesive is used to facilitate intentional removal, the possibilities of accidental detachment are increased. In addition, conventional bags are frequently dimensioned and shaped to have inadequate collection capacity or, if of sufficient size, to become twisted and kinked in use, or become wrapped about the leg of a bedridden patient, thereby increasing patient discomfort and the likelihood of accidental detachment.

It is therefore an object of this invention to provide an improved fecal collector which is accommodated comfortably between the legs of a bedridden patient, has relatively large capacity when considered in terms of its length and collapsed dimensions, and has a highly effective attachment ring that is relatively easy to secure in place and, because of its configuration, conformability, and stretchability, is more likely to remain adhered throughout its intended period of use without causing pain or discomfort when intentional removal is undertaken. Another object is to provide a fecal collector having an adhesive-coated attachment ring that is extendable and contractable, thereby reducing shear forces on the adhesive during body movements and producing more uniform distribution of forces on the attachment ring and bag, all with the result that a more effective sealing engagement may be achieved while at the same time utilizing an adhesive that is not unacceptably aggressive. Other features of the bag, such as the location of the attachment ring and its angular relationship to the rest of the bag, the provision of a protected vent to prevent gas buildup, and the pleated construction of the bag, all contribute, along with the extensibility and flexibility of the attachment ring, in preventing concentration of forces in the areas of adhesive attachment that might result in unintended detachment or leakage of the appliance.

The adhesive-coated attachment ring is formed of a soft, pliable, and stretchable closed-cell thermoplastic foam. In an undeformed state, the ring is generally flat and circular in outline with inner and outer margins that are non-concentric. The adhesive-coated surface has four concentrically-arranged portions, namely, a perineal surface portion intended to seal against the perineal area, a coccygeal surface portion, and a pair of relatively large lateral surface portions. All four portions are covered by individually-removable release sheet sections. Sequential removal of such sheets or sheet sections to dispose the respective adhesive-coated surface portions, starting with the perineal portion, then the coccygeal portion, and finally the lateral portions, greatly facilitates complete and effective adhesive attachment of the ring to a patient.

The bag is formed from a single sheet of odor-barrier film folded upon itself with the folded panels then heat-sealed to each other along their free edges. The attachment ring, or at least a liner for that ring, may be heat sealed to the sheet prior to the sealing of the edges of the side panels to form the finished bag. The capacity of the enlongated bag is significantly increased, without increasing the total length of the bag, by pleating at least one of the side panels prior to the final marginal heat sealing operation.

The bag includes both a vent for the escape of gases and a passage for the insertion of a thermometer or other instrument into the interior of the bag and into direct contact with a patient. It has been found that the passage and vent may be easily and effectively formed by providing each side panel of the bag with a flap or tab portion, then folding such flap portions reversely inwardly into contiguous relation to form a pair of adjacent pockets when the panels are finally heat sealed together and, just before the heat sealing operation, inserting a resilient foam pad into at least one of the pockets. The self-closing passage leading into the interior of the finished bag extends between the contiguous infolded flaps of the pockets. The vent for the escape of gases takes the form of one or more pinholes formed in the wall of a pocket containing the foam pad.

Other features, objects, and advantages of the invention will become apparent from the specification and drawings.

DRAWINGS

FIG. 4 is a side elevational view of the collector.

FIG. 5 is a sectional view taken along line 5—5 of FIG. 4.

FIG. 6 is an enlarged fragmentary sectional view taken along line 6—6 of FIG. 4.

FIG. 7 is an enlarged sectional view taken along line 7—7 of FIG. 4.

FIG. 8 is a sectional view similar to FIG. 7 but illustrating use of the passage for the insertion of a thermometer.

FIG. 9 is an exploded fragmentary perspective view of the attachment ring and release sheet showing the relationship between such elements.

FIGS. 10–12 are a series of simplified and somewhat schematic views illustrating the sequence of steps for properly securing the attachment ring to a patient.

DETAILED DESCRIPTION

Figure 2:
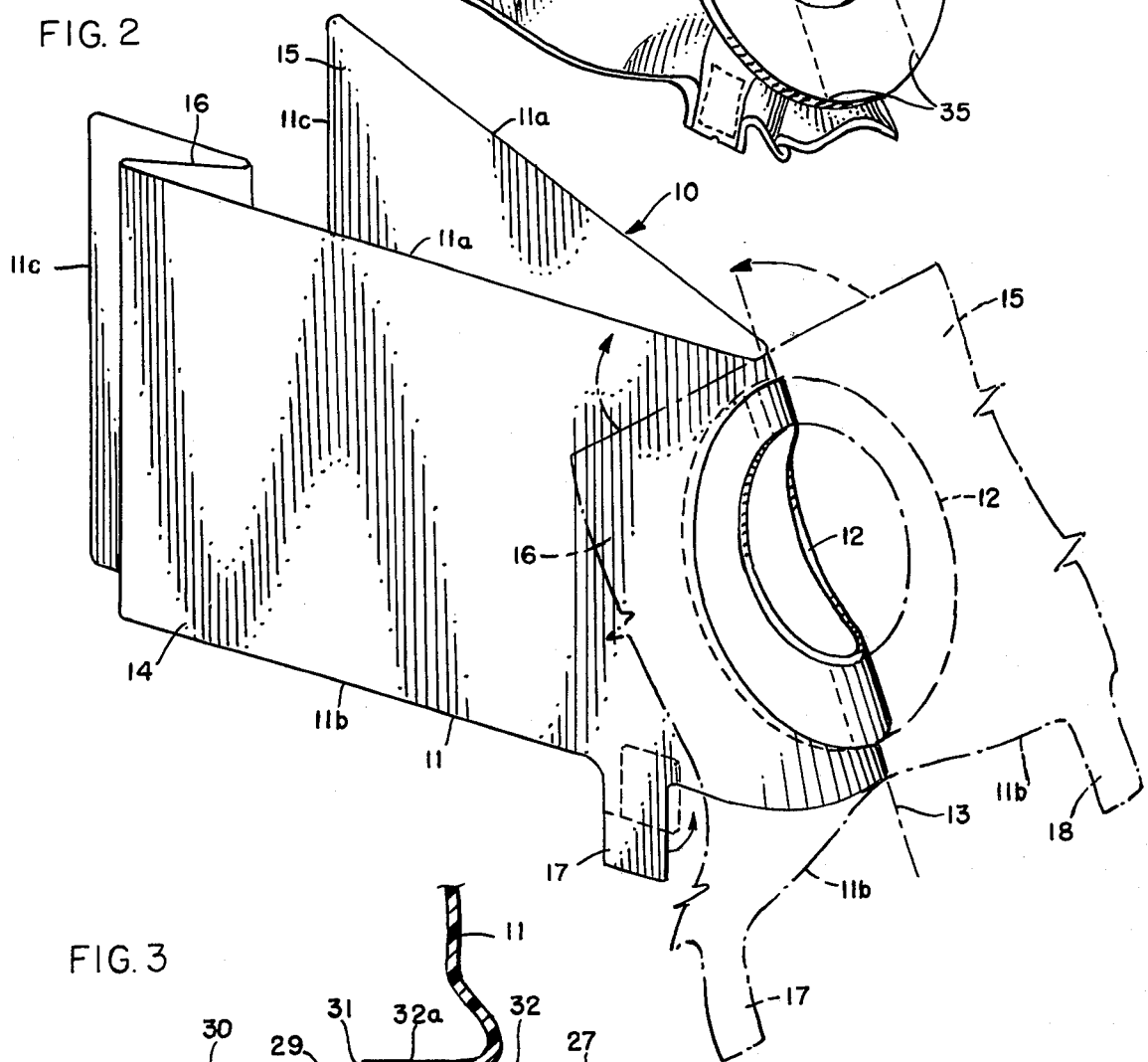
FIG. 2 is a perspective view of the collector showing (in solid lines) the relationship between the side panels of the bag prior to marginal heat sealing and (in broken lines) the relationship between the bag material and the attachment ring at the time such parts are joined together.

Referring to the drawings, the numeral 10 generally designates a fecal collector in the form of a collection bag 11 having an attachment ring 12. In the preferred embodiment depicted, the bag is formed essentially from a single sheet of odor-barrier thermoplastic film folded along vertical midline 13 to provide a pair of contiguous side panels 14 and 15 (FIG. 2). The panels are heat sealed together along their upper, lower, and distal edges 11a, 11b, and 11c, respectively. Just prior to such heat sealing, one or both of the panels may be pleated or folded along generally vertical lines, as shown at 16, to increase the capacity of the bag without adding to its length.

It will be noted from FIG. 2 that each of the lower edges 11b of the side panels is contoured to define a depending tab or flap 17, 18. Prior to heat sealing of the panels, the flaps 17 and 18 are folded upwardly and inwardly to define pockets 17a and 18a, respectively. A foam pad 19 is inserted into one (or both) of the pockets 18a and, during a final heat sealing operation, the panels and flaps are heat sealed together along spaced parallel lines 20 and 21 to define a normally-closed passage 22 (FIGS. 6–8) between the opposed flaps 17 and 18 of the respective panels. Venting means, in the form of one or more pinholes 23, are formed in the wall of the pocket 18a that retains the resilient foam pad 19. The pad performs the functions of restraining the outflow of liquids and solids through vent 23 without at the same time preventing the escape of gases, and of exerting a gentle force against flap 18 to maintain passage 22 in closed condition when not in use (FIGS. 6, 7). To the extent that the excretory contents of the bag may enter and expand pockets 17a and 18a, the walls of passage 22 tend to be sealed even more tightly in use. However, should access to the rectal area become necessary for purposes of inserting a thermometer T or other medical instrument, such a procedure may be carried out without detaching the collector from the patient simply by inserting the instrument through passage 22 (FIG. 8) and into contact with the wearer.

The attachment ring 12 is formed essentially of soft, flexible, and stretchable closed-cell thermoplastic foam having normal planar opposite surfaces 26 and 27 (FIG. 3) and preferably having generally circular outer and inner margins, respectively. A closed-cell foam of polyethylene having a thickness within the general range of 2 to 10 millimeters (preferably about 3 millimeters) has been found particularly effective, other thermoplastic foam materials such as polyurethane, or other suitable plastic sheet materials having the described properties of such foams (i.e., softness, pliability, stretchability, and contractability) might be used.

Figure 3:
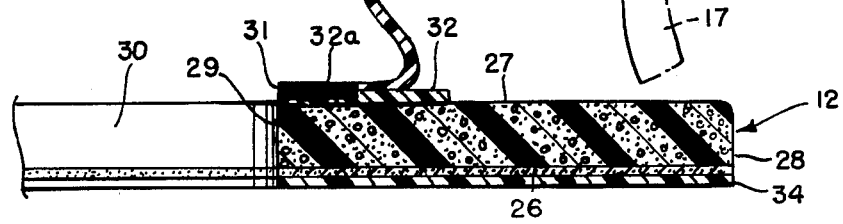
FIG. 3 is an enlarged fragmentary sectional view taken along line 3—3 of FIG. 1.

Surface 26 of foam ring 12 is coated with a layer of pressure-sensitive and water-resistant medically-approved adhesive. The tacky adhesive coating is in turn covered by removable release sheets as will be described in detail hereinafter. The inner margin 29 of the foam ring 12 defines a generally circular aperture 30 that is substantially the same size, and is directly aligned with, opening 31 in one end of the elongated plastic bag 11. The bag and ring may be permanently secured together along the inner margin of the ring in any suitable manner. Since tha bag and ring are both formed of thermoplastic material, the two may be heat sealed together along the inner margin of the ring. However, to avoid deformation of the foam that might occur during heat sealing, it is believed preferable to adhesively secure the bag to the ring as indicated in FIG. 3. Such adhesive attachment is facilitated if a thermoplastic annular liner 32 is first heat sealed to the bag along a heat seal zone 32a extending about opening 31. Thereafter, the outer surface of the annular liner is adhesively bonded to the foam ring 12.

Figure 1:
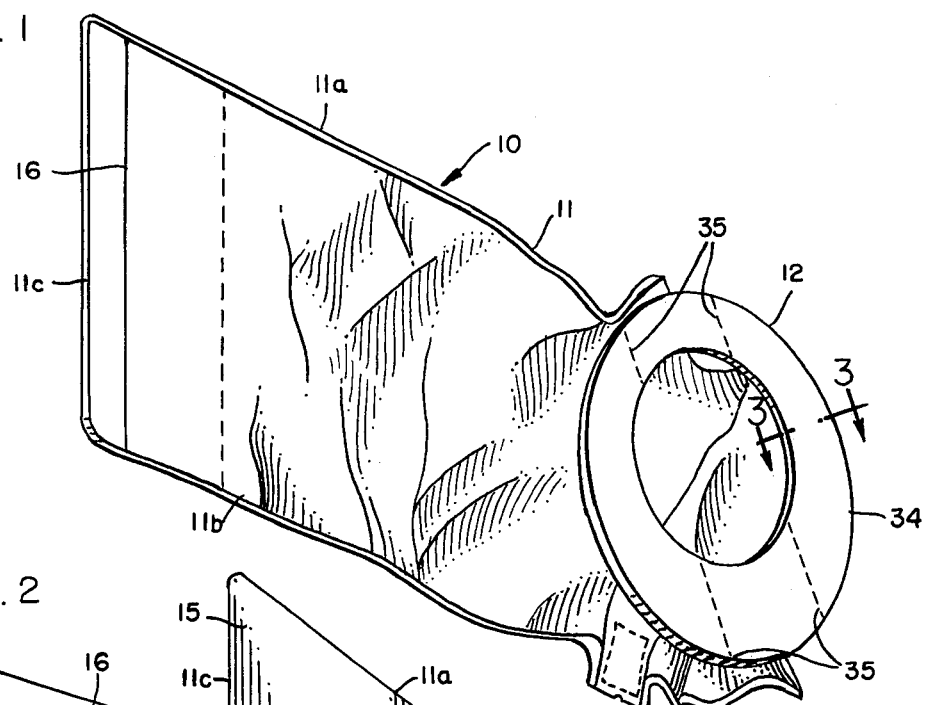
FIG. 1 is a perspective view of a fecal collector embodying the invention.

While the inner and outer margins 29 and 28 of the foam attachment ring 12 are preferably circular, they are not concentric. Specifically, inner margin 29 is displaced upwardly as viewed in FIGS. 1 and 9, or anteriorly in relation to a patient wearing the collection device. The adhesive-covered face 26 of the ring therefore has surface portions of different sizes or areas disposed about aperture 30. Four such portions are depicted in FIG. 9 as demarcated by vertical and parallel phantom lines along face 26. A relatively small perineal zone or portion 26a is located at the upper margin of the ring, such portion having a maximum radial width substantially less than the minimum radial width of the diametrically-disposed coccygeal portion or zone 26b and, as shown in FIG. 9, both the perineal and coccygeal portions are relatively narrow with a horizontal width no greater than that of aperture 30. A pair of lateral portions or zones 26c extend between the perineal and lower coccygeal portions 26a and 26b and, as depicted in FIG. 9, have circumferential or angular dimensions substantially greater than either of the perineal and coccygeal portions.

A removable protective covering 34 extends over the adhesive-coated surface of the foam ring 12. The covering may be formed of paper, suitably coated with a release layer to permit the covering to be peeled away from the adhesive coating of the ring. A polyethylene coating on the paper, to which a silicone coating is applied, has been found effective, but other coating materials such as waxes may be used. As illustrated in FIG. 9, the covering has an overall shape and size conforming with surface 26 of foam ring 12 and is composed of four individually removable sections or portions, namely, a perineal section 34a covering perineal portion 26a of the ring, a coccygeal section 34b over ring portion 26b, and a pair of lateral sections 34c over portions 26c of the foam ring. In the embodiment depicted in the drawings, such sections of the release sheet or covering 34 are defined by two sets of generally parallel lines of perforation or separation 35 that coincide with the phantom lines shown on ring 12 in FIG. 9, that define the lateral limits or boundaries of the narrow perineal and coccygeal portions and the sheet 34 is readily torn along those lines of perforation to permit individual and sequential removal of sections 34a–34c; however, it is to be understood that instead of having perforation lines 35 detachably connecting the several sections of the release sheet, those sections may be completely separated from each other so that no tearing apart is required at the time of sequential removal.

The individually-removable sections 34a–34c of the release sheet, and the particular areas or zones of the adhesive-coated ring surface 26 which they cover, greatly facilitate effective attachment of the foam ring to a patient. In such an attachment procedure, the perineal section 34a is first removed to expose the adhesive-coated perineal surface portion 26a of the ring, and that portion is pressed into firm contact with the perineal area 40 of patient P as somewhat schematically depicted in FIG. 10. During adhesive attachment of the perineal portion 26a of the ring to the perineum of the patient, by pressure applied in the direction of arrow 41, the pliable ring 12 becomes deformed or wedged between the patient's buttocks 42. The coccygeal sheet section 34b is then stripped from the ring (alternatively, it may have been removed from the ring at the time that perineal section 34a was removed) and the exposed adhesive-covered surface of coccygeal ring portion 26b is pressed into contact with the patient's coccygeal area (FIG. 11). It is only after the perineal and coccygeal portions 26a and 26b are firmly secured to the patient, with the ring folded between the buttocks as shown in FIG. 11, that one of the lateral sections 34c is removed to permit one of the side portions 26c of the ring to become adhesively sealed to the patient. The procedure is then repeated by removing the other lateral section 34c of the release sheet and pressing the other adhesive-covered portion 26c of the ring into sealing contact with the patient (FIG. 12). The collection device is thus completely and adhesively sealed to the patient in the perianal area.

The collection bag may be formed of any suitable thermoplastic film or film laminate. For example, flexible walls of the bag may be formed of a polyolefin film laminated with an appropriate gas barrier film. A particularly suitable commercial material comprises low density polyethylene coextruded with a coextensive layer or core of polyvinylidene chloride, but any of a wide variety of other materials may be employed.

While in the foregoing I have disclosed an embodiment of the invention in considerable detail for purposes of illustration, it will be understood by those skilled in the art that many of these details may be varied without departing from the spirit and scope of the invention.

I claim:

1. A fecal incontinence device comprising a pair of panels of thermoplastic sheet material joined at their margins to define an elongated bag having an opening at one end thereof; an attachment ring of soft, pliable, stretchable and contractable plastic material having first and second opposite side surfaces and having outer and inner marginal edges; said inner edge defining an aperture corresponding generally in size and shape with said opening of said bag; said second surface of said ring being secured to said bag about the opening thereof and along a narrow zone adjacent to said inner marginal edge and spaced substantially from said outer marginal edge; said first surface of said ring being coated with a pressure-sensitive adhesive and being composed of a perineal portion, a coccygeal portion, and a pair of lateral portions; and protective release sheet means covering said adhesive coating of said ring; said means comprising a plurality of individually removable sections respectively covering the perineal, coccygeal, and lateral portions of said adhesive-coated surface; said perineal and coccygeal portions being diametrically disposed and extending between said lateral portions; each of said lateral portions having a circumferential dimension substantially greater than each of said perineal and coccygeal portions; said individually removable sections of said protective release sheet means being separable from each other along lines of separation overlying the boundaries between said lateral portions and said perineal and coccygeal portions; said release sheet means having two sets of said lines of separation; whereby, on removal of said perineal and coccygeal sections of said release sheet means, said perineal and coccygeal portions of said ring may be sealed to the perineal and coccygeal areas of a patient prior to removal of said lateral sections of said release sheet means and the sealing of said lateral portions of said ring to such patient.

2. The device of claim 1 in which said bag has a distal end portion opposite from said one end; at least one of said panels being pleated along lines spaced from but adjacent to said distal end for increasing the volumetric capacity of said bag.

3. The device of claim 1 in which said bag is provided with a vent opening along a marginal portion thereof; and a foam pad secured to a wall portion of said bag adjacent to said vent opening.

4. The device of claim 1 in which said inner and outer marginal edges are generally circular and non-concentric.

5. The device of claim 4 in which said two sets of said lines of separation for the individually removable sections of said release sheet means are generally parallel to each other along opposite sides of said perineal and coccygeal portions.

6. The device of claim 5 in which said generally parallel sets of said lines of separation are spaced apart a distance no greater than the horizontal width of the opening defined by the inner marginal edge of said attachment ring.

7. A fecal incontinence device comprising a pair of panels of thermoplastic sheet material joined at their margins to define an elongated bag having an opening at one end thereof; an attachment ring of soft, pliable, stretchable and contractable plastic material having first and second opposite side surfaces and having outer and inner marginal edges; said inner edge defining an aperture corresponding generally in size and shape with said opening of said bag; said second surface of said ring being secured to said bag about the opening thereof and along a narrow zone adjacent to said inner marginal edge and spaced substantially from said outer marginal edge; said first surface of said ring being coated with a pressure-sensitive adhesive and being composed of a perineal portion, a coccygeal portion, and a pair of lateral portions; and protective release sheet means covering said adhesive coating of said ring; said means comprising a plurality of individually removable sections respectively covering the perineal, coccygeal, and lateral portions of said adhesive-coated surface; said bag being provided with a vent opening along a marginal portion thereof; and a foam pad secured to a wall portion of said bag adjacent to said vent opening; said marginal portion with said vent opening comprising a flap portion of one of said panels reversely folded to define a pocket facing into the interior of said bag; said vent opening being located at the folded end of said pocket and said foam pad being disposed within said pocket.

8. The device of claim 7 in which the other of said panels also has a reversely-turned flap portion; said reversely-turned flap portions of the respective panels normally engaging each other but being separable to form a passage therebetween for the insertion of a thermometer or other medical instrument into the interior of said bag.

9. The device of claim 8 in which said foam pad normally urges said first-mentioned flap portion into passage-sealing engagement with said second-mentioned flap portion.

10. A fecal collector comprising a pair of panels of thermoplastic sheet material joined at their margins to define an elongated bag having an opening at one end thereof; a generally flat ring of soft, pliable, stretchable and contractable closed-cell thermoplastic foam having first and second opposing side surfaces and having outer and inner marginal edges; said inner marginal edge defining an aperture aligned with the opening of said bag, and said second surface of said ring being secured to said bag about said opening; said first surface of said ring being coated with a pressure-sensitive water-resistant adhesive; said bag having a distal end opposite from said one end with at least one of said panels pleated along fold lines adjacent to but spaced from said distal end for increasing the volumetric capacity of said bag; said bag being provided with a vent opening along a marginal portion thereof; and a foam pad secured to a wall portion of said bag adjacent said vent opening; comprising a flap portion of one of said panels reversely folded to define a pocket facing inwardly into the interior of said bag; said vent opening being located at the folded end of said pocket and said foam pad being disposed within said pocket.

11. The collector of claim 10 in which said other of said panels also has a reversely folded flap portion; said reversely folded flap portions of the respective panels normally engaging each other but being separable to form a passage for the insertion of a medical instrument into the interior of said bag.

12. The collector of claim 11 in which said foam pad normally urges said first-mentioned flap portion into passage-sealing engagement with said second-mentioned flap portion.

13. A fecal collector comprising a pair of panels of thermoplastic sheet material joined at their margins to define a bag having an opening at one end thereof; a ring of soft, pliable, stretchable and contractable closed-cell thermoplastic film secured to said bag about said opening; said bag being provided with an access port extending between said panels at a zone of separation along the joined margins thereof; and resilient foam pad means secured to an interior wall portion of said bag adjacent said port for urging said panels together at said zone of separation to maintain said port in a normally closed condition.

14. The collector of claim 13 in which said access port is provided in a longitudinal marginal portion of said bag adjacent to said opening of said bag.

15. A fecal collector comprising a pair of panels of thermoplastic sheet material joined to their margins to define a bag having an opening at one end thereof; a ring of soft, pliable, stretchable and contractable closed-cell thermoplastic films secured to said bag about said opening; said bag being provided with a vent opening along a marginal portion thereof; and a resilient foam pad secured to an interior wall portion of said bag adjacent said vent opening; said marginal portion with said vent opening comprising a flap portion of one of said panels reversely folded to define a pocket facing inwardly into the interior of said bag; said vent opening being located at the folded end of said pocket and said foam being disposed within said pocket.

16. The collector of claim 15 in which said other of said panels also has a reversely folded flap portion; said reversely folded flap portions of the respective panels normally engaging each other but being separable to form a passage for the insertion of a medical instrument into the interior of said bag.

17. The collector of claim 16 in which said foam pad normally urges said first-mentioned flap portion into passage-sealing engagement with said second-mentioned flap portion.

* * * * *